United States Patent [19]
Peters et al.

[11] Patent Number: 5,396,303
[45] Date of Patent: * Mar. 7, 1995

[54] SYSTEM AND METHOD FOR PROJECTING AN IMAGE (SUCH AS AN ERG PATTERN) ONTO THE RETINA

[75] Inventors: Daniel R. Peters, Medical Lake, Wash.; John Tabaoda, San Antonio, Tex.

[73] Assignee: American Cyanamid Company, Wayne, N.J.

[21] Appl. No.: 49,903

[*] Notice: The portion of the term of this patent subsequent to Aug. 3, 2010, has been disclaimed.

[22] Filed: Apr. 20, 1993

Related U.S. Application Data

[63] Continuation-in-part of Ser. No. 824,900, Jan. 23, 1992, which is a continuation of Ser. No. 570,123, Aug. 17, 1990, abandoned.

[51] Int. Cl.$^6$ ............................................. A61B 3/10
[52] U.S. Cl. .................................. 351/221; 351/211; 351/246; 128/745
[58] Field of Search ............... 351/200, 205, 211, 216, 351/221, 245, 206, 246; 128/745

[56] References Cited

U.S. PATENT DOCUMENTS

| | | | |
|---|---|---|---|
| 4,266,861 | 5/1981 | Sawa | 351/221 |
| 4,650,302 | 3/1987 | Grant | 351/211 |
| 4,846,568 | 7/1989 | Usui | 351/211 |
| 4,861,154 | 8/1989 | Sherwin et al. | 351/211 |
| 4,867,554 | 9/1989 | Matsumura | 351/211 |
| 5,233,373 | 8/1993 | Peters et al. | 351/221 |

OTHER PUBLICATIONS

Apple, D. J. and Rabb, M. F. (1978) *Clinico pathologic correlations of ocular disease; a text and stereoscopic atlas.* St. Louis, C. V. Mosby. pp. 154–176.

Balazsi, A. G., Drance, S. M., Schulzer, M., Douglas, G. R. (1984) Neuroretinal rim area in suspected glaucoma and early chronic open–angle glaucoma: correlation with parameters of visual function, *Arch Ophthalmol* 102:1011–1014.

Bobak, P., Bodis-Wollner, I., Harnois, C., Maffei, L., Mylin, L., Podos, S., Thornton, J. (1983) Pattern electroretinograms and visual-evoked potentials in glaucoma and multiple sclerosis *Am J Ophthalmol* 96, 72–83.

Marx, M. S., Podos, S. M., Bodis-Wollner, I., Howard-Williams, J. R., Siegel, M. J., Teitelbaum, C. S., Maclin, E. L., Severin, C. (1986) Flash and pattern electroretinograms in normal and . . . *Invest Ophthalmol Vis Sci* 27:378–386, 1986.

Marx, M. S., Podos, S. M., Bodis-Wollner, I., Lee, P., Wang, R., Severin, C. (1988) Signs of early damage in glaucomatous monkey eyes: low spatial frequency losses in the pattern ERG and VEP. *Exp. Eye Res.* 46, 173–184.

Papst, N., Bopp, M., Schnaudigel, O. E. (1984) Pattern electroretinogram and visually evoked cortical potentials in glaucoma *Graefe's Arch Clin Exp Ophthalmol* 222:29–33.

Price, M. J., Drance, S. M., Price, M., Schulzer, M., Douglas, G. R., Tansley, B. (1988) The pattern electroretinogram and visual-evoked potential in glaucoma. *Graefe's Arch Clin Exp ophthalmol* 226:542–547.

Quigley, H. A., Addicks, E. M., Green, W. R., Maumenee, A. E. (1981) Optic nerve damage in human glaucoma. II. The site of injury and susceptibility to damage. *Arch Ophthalmol* 99: 635–649.

Quigley, H. A., Miller, N. R., George, T. (1980) Clinical evaluation of nerve fiber layer atrophy as an indicator (List continued on next page.)

*Primary Examiner*—William L. Sikes
*Assistant Examiner*—David R. Parsons
*Attorney, Agent, or Firm*—Brian R. Woodworth

[57] ABSTRACT

A pattern ERG (PERG) projector includes a coherent light source (32) for generating a projection beam, modulation optics (34) for modulating the projection beam with an alternating ERG interference pattern with a selected spatial and alternation frequency, and wide angle imaging optics (36) for focusing the projection beam such that it passes through the pupil, and then diverges to project onto a selected portion of the retina.

26 Claims, 5 Drawing Sheets

OTHER PUBLICATIONS of glaucomatous optic nerve damage. *Arch Opthalmol* 98:1564–1571.

Quigley, H. A., Sanchez, R. M., Dunkelberger, G. R., L'Hernault, N. L., Baginski, T. A. (1987) Chronic glaucoma selectively damages large optic nerve fibers. *Invest Ophthalmol Vis Sci* 28:913–920.

Sommer, A., Miller, N. R., Pollack, I., Maumenee, A. E., George, T. (1977) The nerve fiber layer in the diagnosis of glaucoma. *Arch Ophthalmol* 95:2149–2156.

Sponsel, W. E. (1989) Tonometry in Question: Can visual screening tests play a more decisive role in glaucoma diagnosis and management? *Surv Ophthalmol 33* (suppl.): 291–300.

Wanger, P. and Persson, H. E. (1983) Pattern–reversal electrograms in unilateral glaucoma. *Invest Ophthalmol Vis Sci* 24: 749–753.

Wanger, P. and Persson, H. E. (1985) Pattern–reversal electro–retinograms in ocular hypertension. *Documenta Ophthalmologica* 61, 27–31.

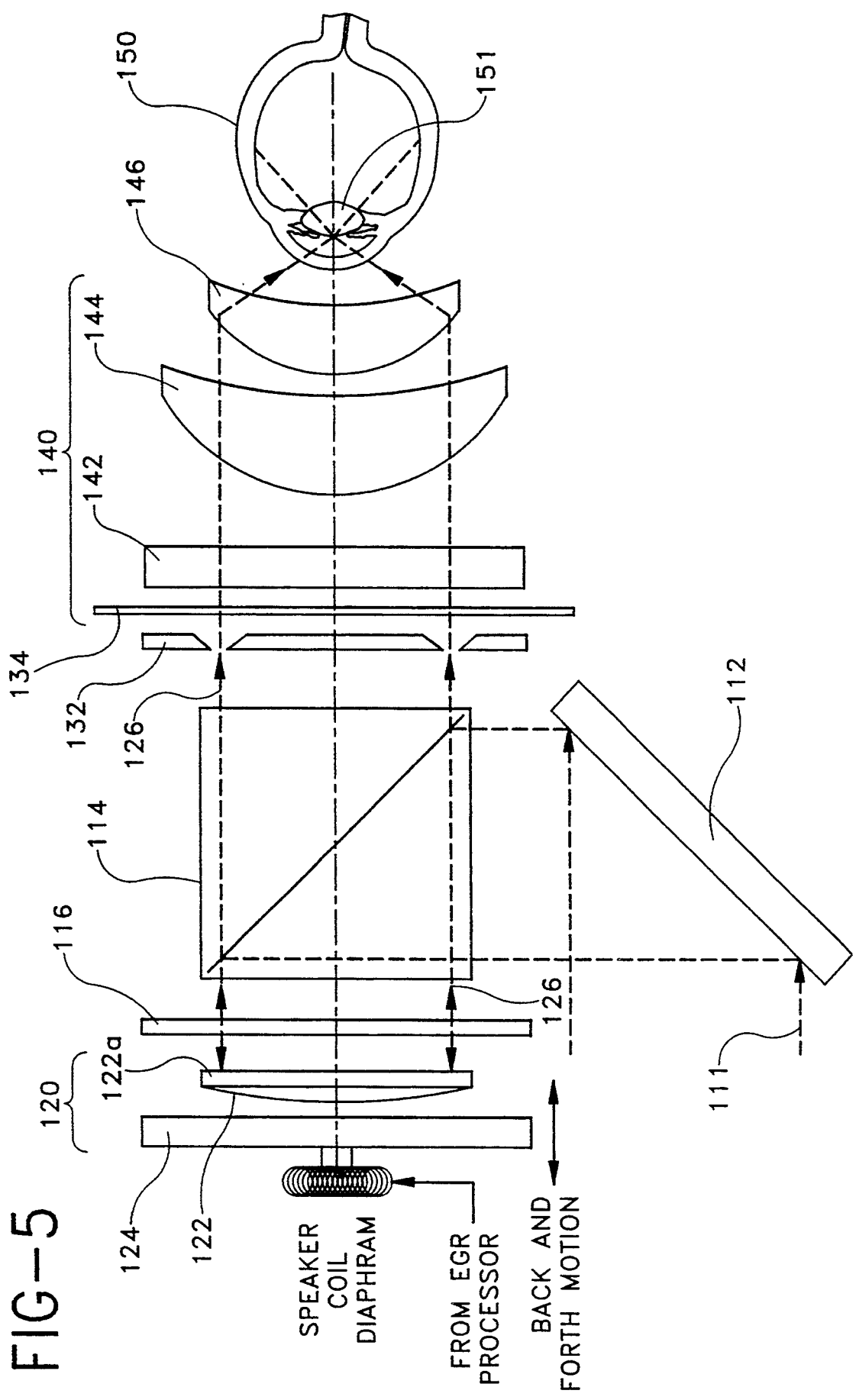

SYSTEM AND METHOD FOR PROJECTING AN IMAGE (SUCH AS AN ERG PATTERN) ONTO THE RETINA

This is a continuation-in-part of U.S. Ser. No. 07/824,900, filed Jan. 23, 1992, which was a continuation of U.S. Ser. No. 07/570,123, filed Aug. 17, 1990, now abandoned.

FIELD OF THE INVENTION

Invention relates to an ophthalmic instrument and a method for projecting an image onto a selected area of the retina. In particular, the invention relates to a pattern electroretinogram (PERG) projector and a method for projecting ERG patterns that can be segmented to probe selected areas of the retina (posterior, medial and/or anterior out to the far periphery) for evaluating retinal degeneration caused by glaucoma and other diseases.

BACKGROUND OF THE INVENTION

As an improved ophthalmic technique for diagnosing and monitoring glaucoma (and other diseases that cause retinal degeneration), electroretinogram (ERG) measurement appears to have considerable promise. Current research indicates that dynamic ERG response to retinal stimulation from an alternating pattern may be a significantly better and earlier indicator of retinal degeneration than conventional intraocular pressure tests, visual field tests, and cup-to-disc ratios.

The specific problem to which the invention can be applied is a pattern electroretinogram (PERG) system capable of assessing the function of the retinal ganglion cell layer and nerve fiber layer, and evaluating retinal degeneration such as for glaucoma diagnosis and management. In addition to permitting the entire retina to be evaluated, the test should have the following features: (1) Sensitivity and specificity; (2) Reproducibility; (3) Ease of use in very young, elderly and disabled patients; (4) Brevity of performance; (5) Easy interpretation; (6) Minimal requirement for patient response and/or attention; (7) Reliability in spite of ocular media opacities; and (8) Freedom from refractive correction.

Ophthalmologists have traditionally relied on relatively few clinical tests and findings to diagnose and follow patients with open angle glaucoma. Recently, the sensitivity of even the most sophisticated tests have been questioned. One recent study has shown that glaucoma suspects may lose up to fifty percent of their optic nerve fibers before developing visual loss detectable by kinetic perimetry (Reference 10, listed at the end of the Background). Moreover, in glaucoma, loss of the nerve fibers and, subsequently, the ganglion cells themselves, have been shown by histopathologic studies (References 1,8,9,11).

Newly developed automated threshold static perimetry has also failed to solve this problem because, in many cases, it is difficult to distinguish progressive visual field loss from short- and long-term fluctuations, as well as from the effects of media opacities and miosis. Additionally, these tests (a) require a significant amount of concentration and participation from patients that is sometimes difficult, (b) require administration by trained personnel, and (c) require a high degree of understanding for accurate interpretation.

Other parameters used to evaluate glaucoma, namely cup to disc (C/D) ratios and intraocular pressures, also have significant disadvantages. Even with the best tools and methods, both inter- and intra-observer variability of the C/D ratio assessment are inevitable (Reference 2). In addition, up to fifty percent of the optic nerve fibers may be lost prior to detectable visual field abnormalities. Elevated Intraocular Pressure (IOP) is well known to be far more prevalent than is open angle glaucoma as defined by visual field loss. In addition, the IOP is extremely variable even in patients with known glaucoma and, as a sole parameter for glaucoma management, is grossly inadequate (Reference 12).

Pattern ERG (PERG) has significant advantages over these current approaches to diagnosing and evaluating retinal degeneration from glaucoma. In PERG, the patient views a pattern image (such as light and dark squares shown on a CRT), and the retina is stimulated by alternating the pattern (such as by light/dark pattern reversal), generating an ERG amplitude response. Many studies have confirmed that the PERG amplitude is significantly reduced in patients with glaucoma (References 3–7,13).

PERG is particularly advantageous because research indicates that the PERG response signal is generated only by the proximal (inner) layers, which are precisely the layers selectively damaged by glaucoma. Thus, PERG has great potential for diagnosing and monitoring retinal degeneration caused by glaucoma (References 3–7,13,14).

Moreover, at least one study has shown that abnormal PERG amplitudes are manifested in patients with only ocular hypertension (i.e. glaucoma suspects) (Reference 14). This group of patients have elevated IOP, but no demonstrable visual field or C/D abnormalities. Many of these patients later go on to develop visual field or C/D abnormalities and hence are diagnosed to have glaucoma. The PERG abnormalities found in these patients suggest that PERG is a more sensitive indicator of early glaucomatous degeneration than are currently utilized tests, at least in some patients.

Conventional PERG has several important advantages: (1) Direct measurement, i.e., minimal cognitive patient response is required for generating PERG data; (2) Brevity, i.e., one pattern alternation generates a corresponding PERG response; and (3) Specificity, i.e., PERG response is generated by the ganglion cells (the retinal component damaged in glaucoma).

However, the current technique for performing PERG measurements based on viewing a CRT pattern has at least two important limitations: (1) It requires an accurate refractive correction to obtain sharp pattern contrast; and (2) It tests only a narrow field-of-view within the posterior retina.

The above-referenced field-of-view limitation, i.e., a field-of-view limited to the posterior-most regions of the retina, is particularly disadvantageous because the posterior retina survives best to the final stage of glaucoma, while the ganglion cells in the more anterior regions of the retina are frequently lost first. This phenomenon of glaucomatous damage is demonstrated by the generalized constriction seen on standard visual field testing of patients with glaucoma. This pattern of vision loss progresses until only a central island of vision remains, and it is precisely this most resistant region that is being stimulated by a standard PERG.

The entire retina can be stimulated by a flash ERG (FERG) procedure. In a standard flash ERG (FERG), a flash of light generates a dynamic ERG amplitude response caused by the stimulation of both the distal (photoreceptor) and proximal (ganglion) layers of the retina in all retinal regions (posterior, middle and anterior). This mass retinal response is of no advantage in monitoring glaucomatous retinal degeneration, which selectively affects only the nerve fibers and their parent ganglion cells.

Systems employing laser interferometers and potential acuity meters have been used to evaluate visual acuity in some subjects. However, the interferometer projects an interference pattern, while the potential acuity meter projects an eye chart. Thus, these projection systems have not been used for PERG testing, and are capable only of projecting into limited areas of the posterior retina.

Accordingly, a specific need exists for a PERG system capable of stimulating the posterior, medial, and anterior portions of the retina. A more general need exists for an ophthalmic instrument for projecting images (modulated light) onto a selected area of the retina.

REFERENCES

1. Apple, D. J. and Rabb, M. F. (1978) Clinico pathologic correlations of ocular disease; a text and stereoscopic atlas. St. Louis, C. V. Mosby.
2. Balazsi, A. G., Drance, S. M., Schulzer, M., Douglas, G. R. (1984) Neuroretinal rim area in suspected glaucoma and early chronic open-angle glaucoma: correlation with parameters of visual function. Arch Ophthalmol 102:1011–1014.
3. Bobak, P., Bodis-Wollner, I., Harnois, C., Maffei, L., Mylin, L., Podos, S., Thornton, J. (1983) Pattern electroretinograms and visual-evoked potentials in glaucoma and multiple sclerosis. Am J Ophthalmol 96, 72–83.
4. Marx, M. S., podos, S. M., Bodis-Wollner, Howard-Williams, J. R., Siegel, M. J., Teitelbaum, C. S., Maclin, E. L., Severin, C. (1986) Flash and pattern electroretinograms in normal and laser-induced glaucomatous primate eyes. Invest Optlthalmol Vis Sci 27:378–386, 1986.
5. Marx, M. S., podos, S. M., Bodis-Wollner, I., Lee, P., Wang, R., Severin, C. (1988) Signs of early damage in glaucomatous monkey eyes: low spatial frequency losses in the pattern ERG and VEP. Exp. Eye Res. 46, 173–184.
6. Papst, N., Bopp, M., Schnaudigel, O. E. (1984) pattern electroretinogram and visually evoked cortical potentials in glaucoma. Graefe's Arch Clin Exp Ophthalmol 222:29–33.
7. Price, M. J., Drance, S. M., price, M., Schulzer, M., Douglas, G. R., Tansley, B. (1988) The pattern electroretinogram and visual-evoked potential in glaucoma. Graefe's Arch Clin Exp Ophthalmol 226:542–547.
8. Quigley, H. A., Addicks, E. M., Green, W. R., Maumenee, A. E. (1981) Optic nerve damage in human glaucoma. II. The site of injury and susceptibility to damage. Arch Ophthalmol 99:635–649.
9. Quigley, H. A., Miller, N. R., George, T. (1980) Clinical evaluation of nerve fiber layer atrophy as an indicator of glaucomatous optic nerve damage. Arch Opthalmol 98:1564–1571.
10. Quigley, H. A., Sanchez, R. M., Dunkelberger, G. R., L,Hernault, N. L., Baginski, T. A. (1987) Chronic glaucoma selectively damages large optic nerve fibers. Invest Ophthalmol Vis Sci 28:913–920.
11. Sommer, A., Miller, N. R., Pollack, I., Maumenee, A. E., George, T. (1977) The nerve fiber layer in the diagnosis of glaucoma. Arch Ophthalmol 95:2149–2156.
12. Sponsel, W. E. (1989) Tonometry in Question: Can visual screening tests play a more decisive role in glaucoma diagnosis and management? Surv Ophthalmol 33 (suppl): 291–300.
13. Wanger, P. and Petsson, H. E. (1983) Pattern-reversal electroretinograms in unilateral. glaucoma. Invest Ophthalmol Vis Sci 24:749–753.
14. Wanger, P. and Persson, H. E. (1985) Pattern-reversal electroretinograms in ocular hypertension. Documenta Ophthalmologica 61, 27–31.

SUMMARY OF THE INVENTION

The present invention is directed to a retinal projection system and method for projecting an image onto a selected area of the retina with a field-of-view that includes retinal areas anterior to the posterior 25° of the visual field of the retina. In one aspect of the invention, the retinal projection system includes a light source for generating a projection beam which is at least partially coherent. Modulation optics modulate the projection beam with a desired image, and wide angle imaging optics adjacent the eye focus the modulated projection beam, such that the projection beam passes through the pupil and diverges to provide a predetermined field-of-view. By appropriately controlling the wide angle focusing optics, the field-of-view can be adjusted to include the medial and anterior sections of the retina, including the far periphery.

In another aspect of the invention, the retinal projection system is used as a pattern ERG (PERG) projector for evaluating retinal degeneration caused by glaucoma or other disease. The PERG projector includes imaging optics to project an ERG pattern onto a selected area of the retina that includes an area anterior to the posterior 25° of the field-of-view of the retina.

In more specific aspects of the invention, an exemplary PERG projector includes imaging optics that provide wide angle projection of an alternating, selectively segmented ERG interference pattern, enabling the entire retina to be probed. Interferometry modulation optics modulate the projection beam with an ERG interference pattern characterized by a selected fringe line spacing, and selectively alternate the interference pattern to create the ERG pattern shift that stimulates an ERG response. Segmentation optics allow the ERG pattern to be selectively segmented for stimulating a selected area of the retina, including an area anterior to the poster 25° of the field-of-view of the retina.

In one embodiment, the interferometry optics comprise a shearing interferometer. A pair of prisms are separated by a gap defined by opposing non-parallel surfaces that define a shearing angle. One of the prisms is pivotally mounted for selectively changing the shearing angle to provide precision angle tuning of the interference pattern. The incident projection beam partially reflects from one opposing prism surface, and after transiting the prism gap, partially reflects from the opposing prism surface. The two reflected projection beams interferometrically combine to form an interference pattern. The prism gap is filled with a Kerr fluid and the opposing prism surfaces are coated with transparent conductive electrode layers, such that an adjustable time varying electric field can be used to change the refractive index in the prism gap, and alternate (reverse) the interference pattern.

In another embodiment, the interferometry optics include a plano convex lens and a reflective optical flat. The lens has an antireflective coating on a flat side so that it partially reflects and partially transmits the incident projection beam. The reflective optical flat reflects the transmitted portion of the incident projection beam back through the plano convex lens, thereby creating an interference pattern with the two reflected projection beams. The optical flat can be selectively translated to shift the interference pattern.

The wide angle imaging optics can be formed by an aspheric parabolic lens, followed by a positive meniscus lens. The lenses are configured to allow the projection beam to be brought to a sufficiently sharp focus in the area of the eye lens to transmit through even a constricted pupil, and then to diverge to fill substantially the entire field-of-view of the retina.

As an alternate application, the retinal projection system can be used to project video or printed information directly into the eye. In this application, the modulation optics can be formed by a LCD video panel.

The technical advantages of the invention include the following: (1) The retinal projection system can be used to project selected images, including video, text and other information, onto the retina with a field-of-view that can extend significantly anterior to the posterior area of the retina. (2) Laser light can be used for projection to bypass potential ocular media opacities, and to obviate the need for any refractive correction. (3) In a PERG application, an ERG pattern (such as an alternating interference pattern) can be projected into any selected area of the retina (posterior, medial and/or anterior out to the far periphery), providing the ability to test the retinal elements damaged by glaucoma in the areas where they are most likely to be affected first (i.e., the ganglion cells in the anterior retina and especially in the periphery). (4) The ERG pattern can be selectively segmented to probe selected areas of the retina, allowing a retinal map to be developed for the entire retinal field, and allowing the different retinal regions to be compared to each other. (5) The ERG interference pattern can be modulated both spatially (spatial frequency or fringe line spacing) and temporally (alternation frequency).

For a more complete understanding of the invention, and for further features and advantages, reference is now made to the following Detailed Description of the invention, taken in conjunction with the accompanying Drawings. Although the Detailed Description, and the Drawings, are provided with respect to specific, exemplary embodiments of the invention, various changes and modifications may be suggested to one skilled in the art, and it is intended that the invention encompass such changes and modifications as fall within the scope of the appended claims.

BRIEF DESCRIPTION OF THE DRAWING

FIG. 5 illustrates an alternative embodiment using a Newton's ring interferometer to generate an ERG interference pattern.

DETAILED DESCRIPTION OF THE INVENTION

The Detailed Description of exemplary embodiments of the retinal projection system of the invention is organized as follows:
1. Retinal Projection Technique
2. Exemplary PERG Projector
   2.1. Laser Light Source
   2.2. Interferometry Modulation Optics
   2.3. Segmentation Optics
   2.4. Wide Angle Imaging Optics
   2.5. ERG Detection System
   2.6. PERG Program
   2.7. Alternate Interferometry Optics
3. Alternate Applications While the Detailed Description is provided in relation to an exemplary application of the retinal projection system as a pattern electroretinogram projector, such as for use in evaluating and treating glaucoma, the invention has general applicability to projecting images (modulated light) onto the retina with a field-of-view that can be extended into areas anterior to the posteriormost portions of the retina, including the periphery.

1. Retinal Projection Technique

Figure 1:
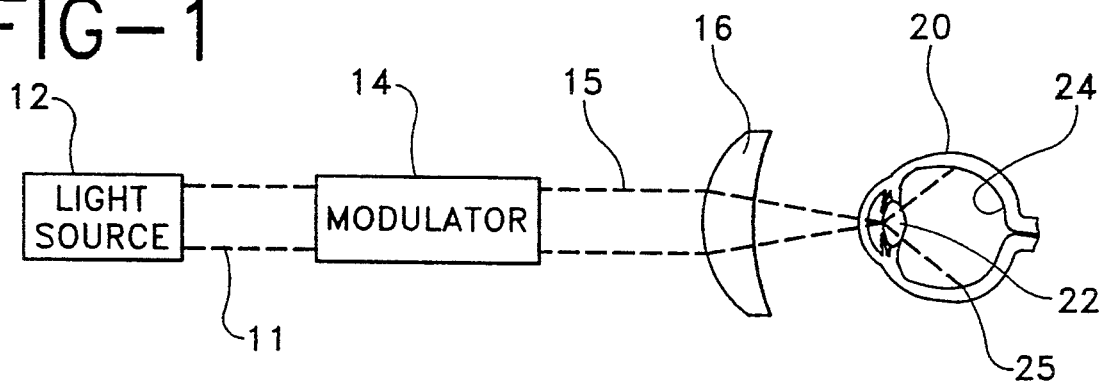
FIG. 1 is a functional block diagram of the retinal projection system of the invention.

FIG. 1 illustrates the retinal projection technique of the invention. A projection beam 11 is generated by a light source 12 that is at least partially coherent. The light is modulated by modulation optics 14 to form a modulated projection beam 15 with the desired pattern or image.

The modulated projection beam 15 is input to wide angle imaging optics 16 adjacent to the eye 20. The wide angle imaging optics bring the modulated projection beam to a sharp focus in the area of the eye lens 22, enabling the beam to pass through a constricted pupil. After passing through the pupil, the beam diverges rapidly within the eye and is projected onto the entire retina 24 or any preselected portion thereof. That is, the retinal projection technique of the present invention enables a pattern or other image to be projected with a field-of-view that includes the anterior, medial and/or posterior areas of the retina, including the far periphery regions 25. In one embodiment of the present invention, the field-of-view includes an area anterior to the posterior 25° of the retina, thereby facilitating earlier detection of glaucoma and other diseases.

2. Exemplary PERG Projector

The exemplary PERG projection system provides wide angle ERG pattern projection onto the entire retina or any preselected portion thereof. The ERG pattern can be selectively segmented to probe selected areas of the retina for degeneration caused by glaucoma or other diseases.

Figure 2:
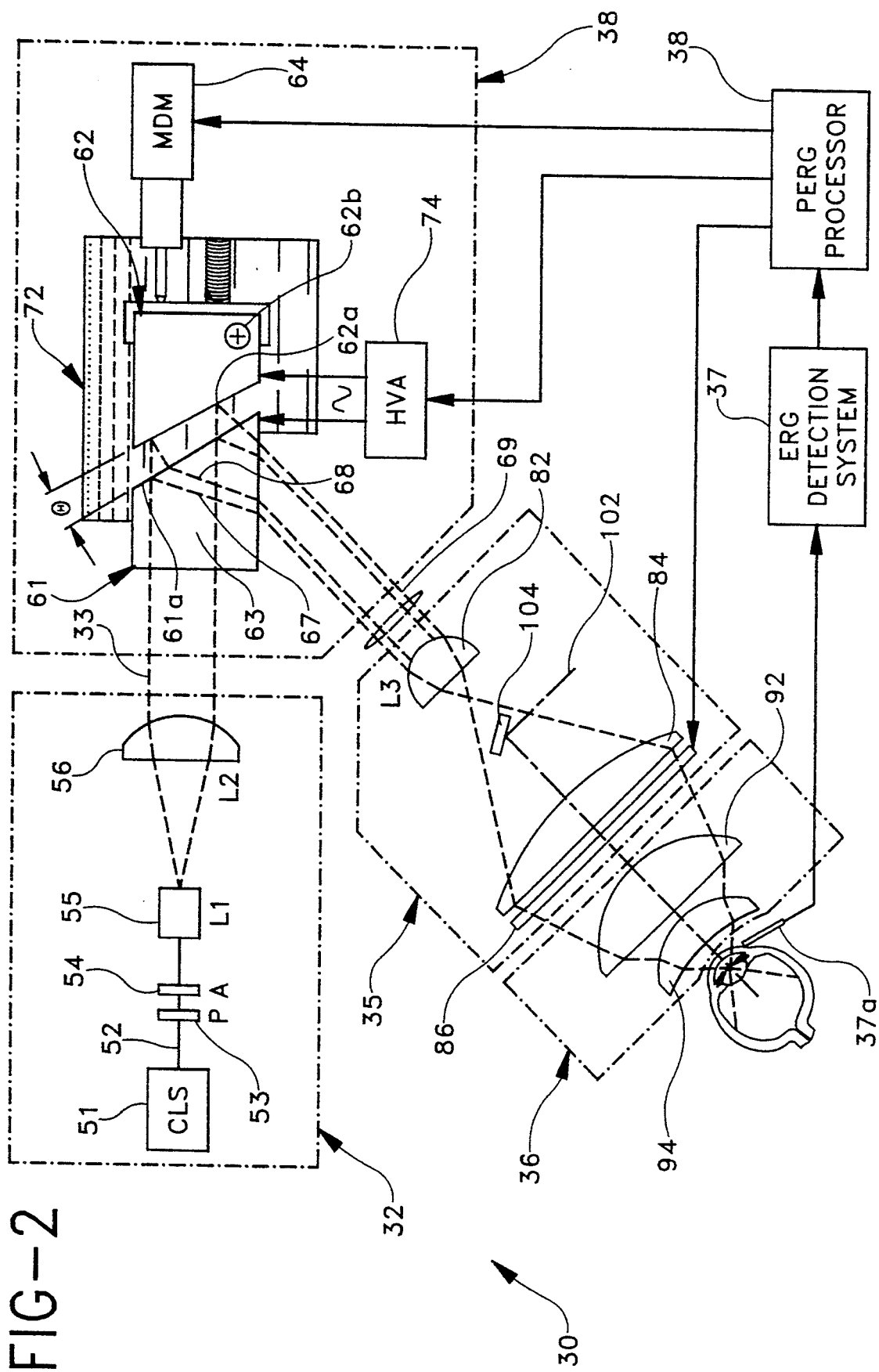
FIG. 2 illustrates an application of the retinal projection system as a PERG projector capable of projecting an ERG pattern onto the entire field-of-view of the retina, including a shearing interferometer for generating an ERG interference pattern.

FIG. 2 illustrates an exemplary embodiment of the PERG projector 30, including a laser light source 32 for providing a coherent projection beam 33, modulation optics 34 for generating a PERG interference pattern, segmentation optics 35 for selectively segmenting the PERG pattern, and wide angle imaging optics 36 for imaging the PERG pattern onto the retina. The ERG response is detected by an ERG detection system 37 that includes at least one ERG electrode 37a.

A PERG processor 38 controls modulation optics 34 and segmentation optics 35 to produce the desired interference pattern and the desired segmentation. PERG processor 38 also receives the resulting ERG responses from the ERG detection system 37.

The limits of the normal visual field upon maximum target stimulation measure approximately 60° above and nasal of center, 70° below center, and 100° temporal of center, thereby creating a normal full visual field that can be depicted as a horizontal oval identified 200 in FIG. 8. A central visual field 202 is commonly defined by drawing an arc 60° from the axis normal to the posterior-most point of the retina 212, thus creating a circular 120° field. The posterior region 204 of retina commonly is defined between 0° and 40° while the medial region 206 and the anterior region 208 commonly are defined between 40°-80° and 80°- 120°, respectively. Regions lying beyond the central visual field 202 are referred to as peripheral.

Figure 3:
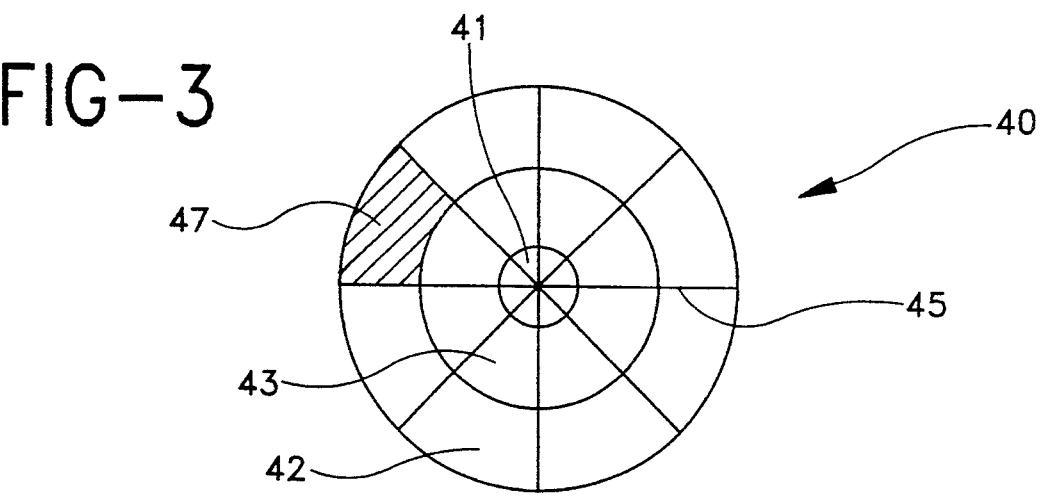
FIG. 3 illustrates an exemplary segmentation of the ERG pattern from the PERG projector, to allow selected segments of the entire retina to be probed.

FIG. 3 illustrates an exemplary segmentation of the retina. The entire field-of-view for the retina is represented by a circle 40 divided into seventeen representative segments. The retinal field-of-view is separated into concentric posterior 41 and anterior 42 regions, separated by a medial region 43. In addition, the field-of-view in the anterior and medial regions is sectored by radial sector lines 45, defining segments such as 47.

The PERG processor executes a PERG program to control the modulation optics 34 and the segmentation optics 35, thereby determining the retinal segments (regions and sectors) stimulated by the PERG, and the spatial and temporal frequencies for the projected ERG pattern. As a result, the retinal segments can be selectively probed to develop an accurate map of the entire retinal field. Using this retinal map, the retina can be evaluated for degeneration caused by glaucoma (or other disease).

2.1. Laser Light Source

Referring to FIG. 2, light source 32 includes a laser 51 (such as helium, neon, or argon) that generates a projection beam 52 of coherent light. Alternatively, a point source of light could be used to provide a projection beam of at least partially coherent light.

The projection beam is directed through a polarizer 53 and an analyzer 54, which are configured as polarized sheets. The projection beam 52 is adjusted in intensity by rotating the polarizer relative to the plane of polarization established by the analyzer.

The projection beam is expanded by a lens 55, recollimated by a lens 56, and directed toward modulation optics 34.

The intensity of the laser light can be controlled to maintain a comfortable and safe level, but sufficient to induce an ERG response.

2.2. Interferometry Modulation Optics

In one embodiment of the present invention, modulation optics 34 comprise a shearing interferometer. Alternate interferometer configurations are described in Section 2.7. Other suitable interferometers include, but are not limited to, the Michaelson, the Mach Zender, and the Twyman-Green interferometers (see Section 2.7).

The exemplary shearing interferometer depicted in FIG. 2 includes two prisms 61 and 62 with respective opposing partially reflecting surfaces 61a and 62a separated by a gap 63. The prisms are mounted such that the reflecting prism surfaces are non-parallel and such that the prism surfaces define a shearing angle Theta.

The incident projection beam 33 enters prism 61 and is partially reflected from prism surface 61a to provide a first reflection beam 67. The portion of incident projection beam 33 not reflected from prism surface 61a is transmitted across gap 63, and a portion of this beam is reflected from prism surface 62a, back across gap 63 to provide a second reflection beam 68.

The first and second reflection beams 67, 68 combine interferometrically into a PERG interference beam 69, producing an ERG interference pattern of light and dark fringe lines. The PERG pattern is controlled in spatial frequency (i.e., the fringe line spacing) by the shearing angle Theta.

In the embodiment of the present invention depicted in FIG. 2, prism 61 is stationary while prism 62 is spring-loaded and pivotally mounted at a pivot point 62b. Prism 62 can be selectively pivoted by a motor-driven micrometer 64. Pivoting micrometer 64 is responsive to control signals from PERG processor 38 to control the shearing angle Theta between non-parallel prism surfaces 61a and 62a, providing precision angle tuning of the spatial frequency for the interference pattern.

To implement the pattern shifting required to produce a PERG response, the PERG interference pattern is alternated through a light-dark cycle with a selected frequency of alternation. Interferometer prisms 61 and 62 are at least partially immersed in a Kerr cell 72 filled with a Kerr fluid (such as carbon disulfide), such that the Kerr fluid fills the gap 63 between the prisms.

The opposing prism surfaces 61a and 62a are coated with a transparent conductive material such as indium-tin-oxide. The conductive coatings are coupled to a high voltage amplifier 74.

The high voltage amplifier receives a low frequency 120 Hz signal from PERG processor 38. As a result, an electric field is established in the gap 63 and applied to the Kerr fluid, thereby changing the refractive index of the Kerr fluid. Thus, by controlling the electric field in the gap, the effective path length through the gap for the second reflection beam 68 can be changed. This path modulation results in a selective shift in the light-/dark areas of the interference pattern.

The PERG interference beam 69, modulated with an interference pattern characterized by a selected angle tuned spatial frequency, and a selected alternation frequency, is directed to segmentation optics 35.

2.3. Segmentation Optics

Segmentation optics 35 provide the desired segmentation for the projected ERG pattern. The time-varying PERG interference beam 69 is first expanded by lenses 82 and 84 and then directed through a spatial light modulator 86.

The exemplary spatial light modulator 86 is conventionally formed by liquid crystal films sandwiched between transparent electrode plates. The modulator is configured to provide the segmentation of the retinal field-of-view illustrated in FIG. 3.

In response to control signals from PERG processor 38, spatial light modulator 86 selectively passes the entire time-varying PERG interference beam 69 (i.e., the entire ERG interference pattern), or any selected segment. For example, the modulator could be controlled to pass the ERG interference pattern only into the anterior region (42 in FIG. 3), or only into one or more sectors of that region (47 in FIG. 3).

As set forth in the Background of the Invention, it is preferable that the ERG interference pattern passes into more than just the most posterior sections of the retina in order to facilitate earlier diagnosis of glaucoma. Thus, in one embodiment of the present invention, at least a portion of the PERG interference pattern is directed to a portion of the retina anterior to the posterior-most 25° of the field-of-view, thereby providing ERG responses in such regions. The posterior-most 25° of the retina is identified as area 210 in FIG. 8.

Figure 8:
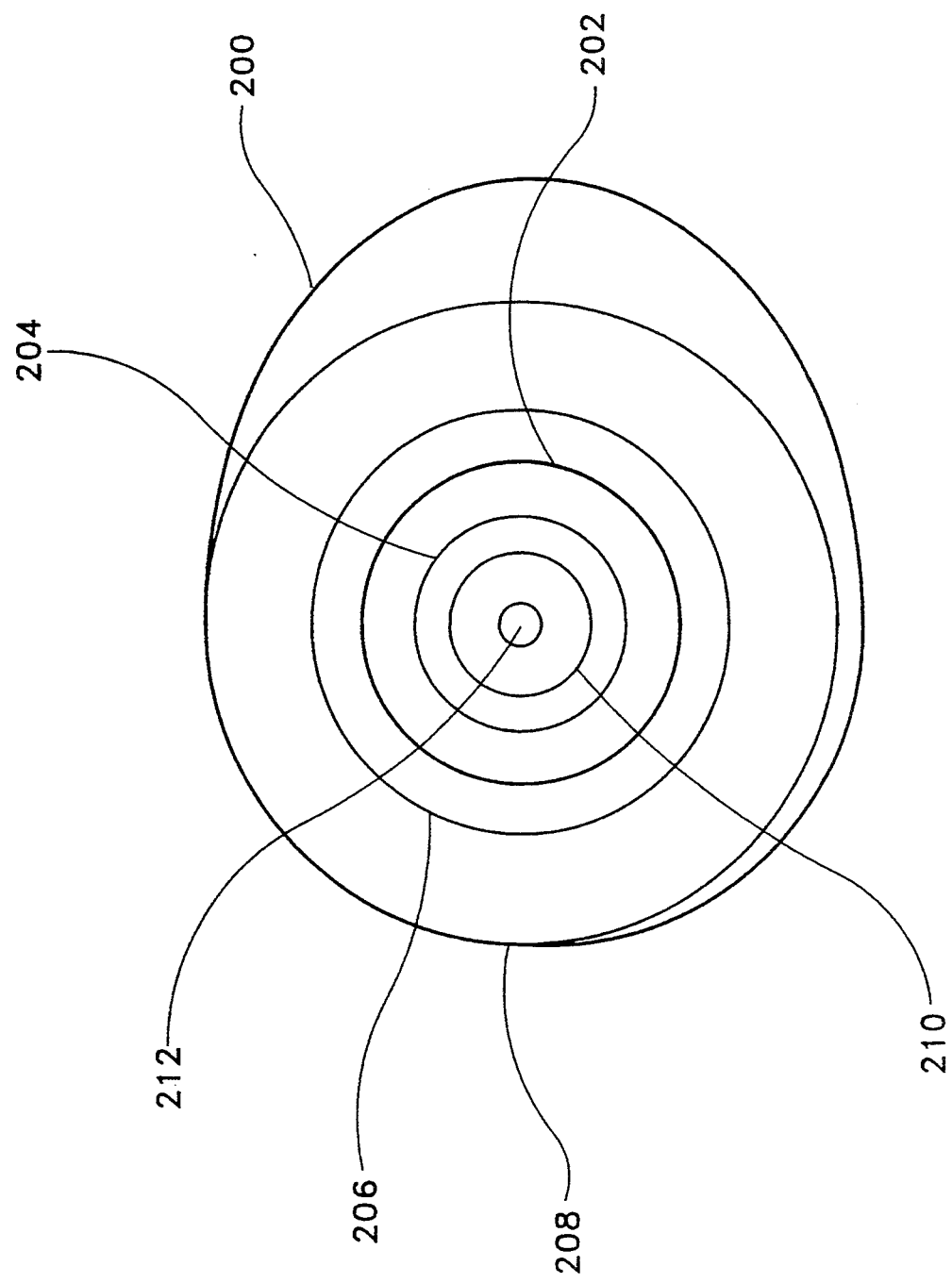
FIG. 8 depicts a map of the normal visual field of the retina.

By way of example and not by way of limitation, the present invention can be used to diagnose retinal diseases such as glaucoma in the posterior region of the retina, i.e., those areas lying within a 40° zone as indicated at 204 in FIG. 8. In this application of the present invention, the projection beam preferably is focused such that at least a portion of the beam is projected onto the retina at a position 25°–40° from the posterior-most point of the retina, identified at 212 in FIG. 8, in order to ensure that ERG responses are generated throughout a representative section of the posterior retina. By focusing the projection beam to include this area, earlier diagnosis of glaucoma is possible, as discussed above. Similarly, if the present invention is used to diagnose retinal diseases in the medial region of the retina, it is preferable that at least a portion of the projection beam is projected onto the retina at a position 40°–80° from the posterior-most point 212 of the retina. Finally, if the present invention is used to diagnose retinal diseases in the anterior retina, at least a portion of the projection beam is projected onto the retina at a position 80°–120° from the posterior-most point 212 of the retina. It is to be appreciated that the present invention can be used to project a projection beam to the entire field-of-view of the retina, including the peripheral areas, thereby facilitating the diagnosis of disease throughout the retina.

After selective segmentation, the time-varying PERG interference beam is directed to the wide angle imaging optics 36.

2.4. Wide Angle Imaging Optics

For the exemplary PERG system, wide angle imaging optics 36 project the PERG interference beam into the eye, projecting the segmented ERG pattern into the entire field-of-view of the retina, or to any preselected area. Wide angle imaging optics 36 preferably include two lenses 92, 94 located adjacent, but not in contact with, the eye. Parabolic aspheric lens 92 preferably has a back focal length of about 30 mm, whereas positive meniscus lens 94 preferably has a focal length of about 60 mm. Parabolic lens 92 is made aspheric to correct for spherical aberration. Alternatively, a contact lens could be used for at least a portion of the imaging optics.

The incident PERG interference beam is brought to a sharp focus at the eye lens such that the beam can pass through a constricted pupil. The beam then diverges to project onto the entire retina, filling the field-of-view out to the far periphery or filling any preselected area of the retina.

Since the projected PERG beam is collimated, it does not depend on the accommodation of the subject eye. Also, if any lens opacity exists, it can be circumvented to some extent by focal point adjustment.

A suitable fixation beam 102 may be directed into the eye along the optical axis by a micro-miniature mirror 104. During the PERG test, the patient fixates on the fixation spot while the PERG processor executes a PERG program.

If it is desired to project the PERG beam only into the posterior retina, zoom optics such as described in Section 2.6 can be included in the optical path to control the diameter of the projected PERG pattern. Alternatively, imaging optics that do not provide for wide angle projection can be used. However, as set forth in detail above, in one embodiment of the present invention, the PERG beam is projected such that at least a portion of the beam is directed to an area of the retina that is anterior to the posterior-most 25° of the retina.

The resulting electrophysiological signal from the eye is detected by ERG detection system 37, and a corresponding ERG response is provided to the PERG processor 38.

2.5. ERG Detection System

The ERG detection system 37 converts the electrophysiological ERG response from the eye to a corresponding digital ERG response for input to the PERG processor.

The electrophysiological ERG response is detected by an electrode 37a, such as a fine gold leaf placed beneath the lower eye lid. Alternatively, the electrode may be placed on a part of a contact lens.

The electrophysiological ERG response is input to ERG detection system 37. The ERG detection system operates conventionally in providing signal amplification and analog-to-digital conversion, outputting a corresponding digital ERG response signal.

2.6. PERG Program

Figure 4:
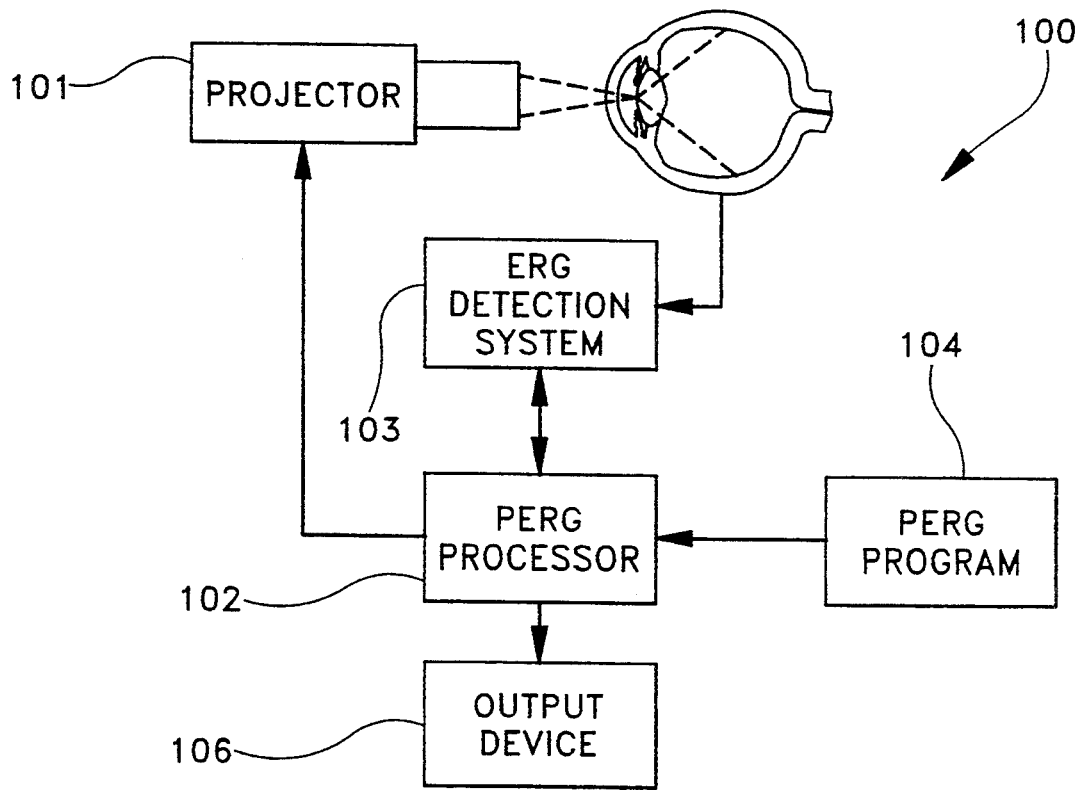
FIG. 4 is a functional block diagram of a PERG performing under computer control PERG testing using a PERG projector according to the invention.

FIG. 4 is a functional diagram illustrating a PERG system 100 for implementing a processor controlled PERG program. This PERG program is a routine extension of the conventional approach to acquiring PERG data.

A PERG projector 101 according to the invention is coordinated with a PERG processor 102. The PERG projector receives pattern control signals from the PERG processor, creating a desired ERG interference pattern that is projected onto the retina. Specifically, the PERG processor provides pattern modulation signals that control spatial frequency (pattern fringe line spacing) and alternation frequency (pattern phase shifting). Thus, for a given fringe line spacing, the program-determines how frequently the interference pattern is shifted to produce an ERG response.

The resulting ERG electrophysiological response is acquired by an ERG detection system 103. The ERG detection system is controlled by the PERG processor, which receives the ERG response data.

A PERG program 104, executed by the PERG processor, carries out a series of PERG pattern tests using segmented patterns to probe the retina, and to develop an ERG response map of the entire retinal field. Using the retinat map, an ERG analysis is performed by the PERG processor and reported in an output device 106.

2.7. Alternate Interferometry Optics

Figure 6:
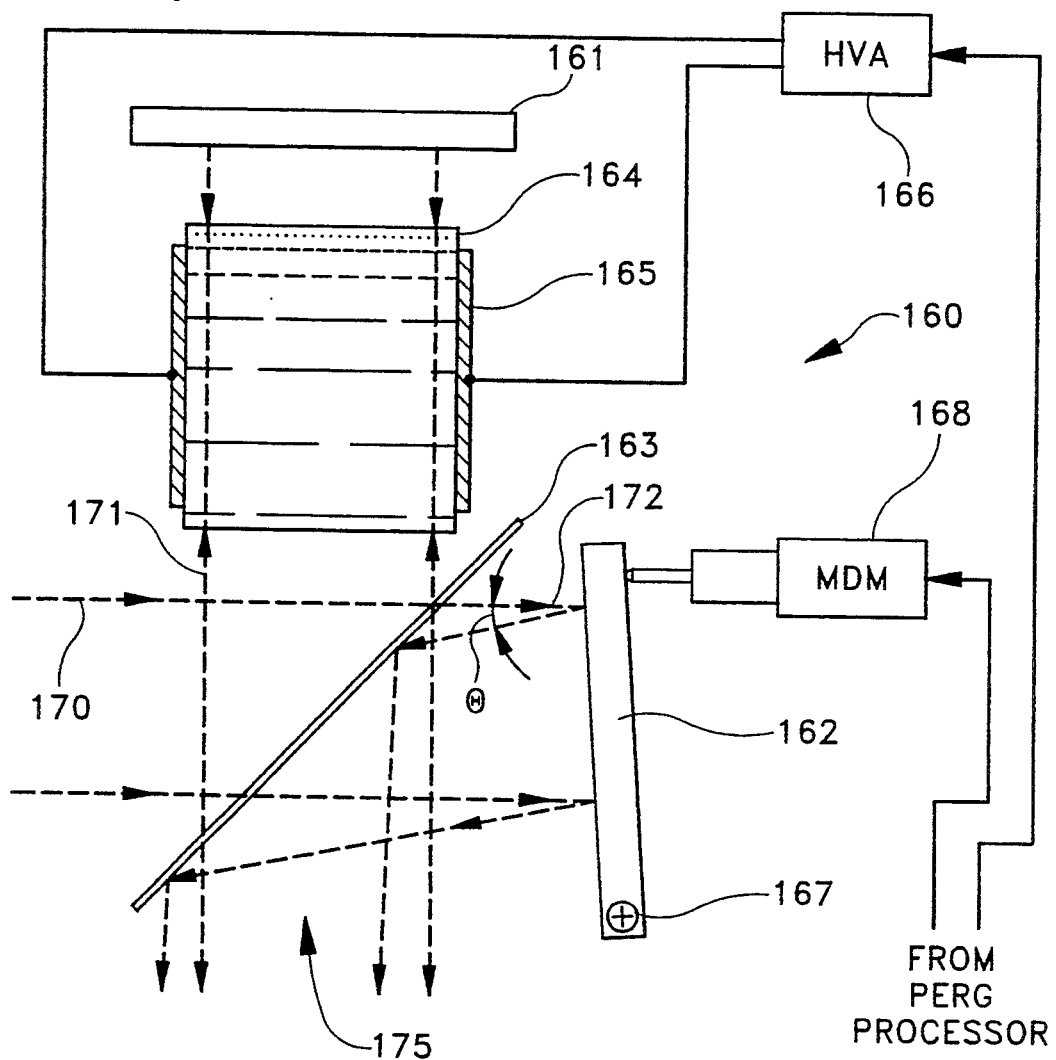
FIG. 6 illustrates an alternative embodiment of the interferometry optics using a Michaelson interferometer.
Figure 7:
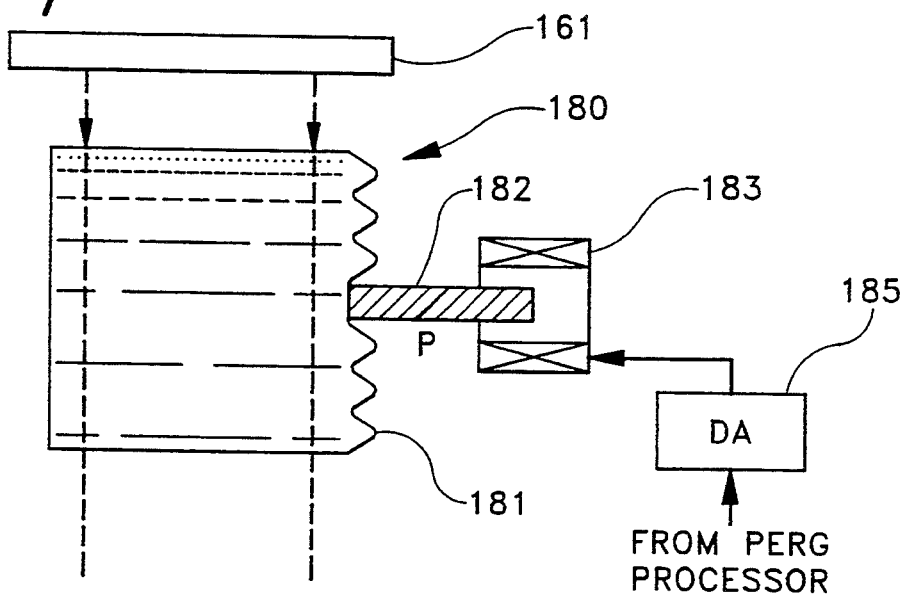
FIG. 7 illustrates an alternative embodiment of the interferometry optics using a pressure driven interferometer.

FIGS. 5, 6 and 7 illustrate alternative embodiments of the interferometry optics used to modulate the projection beam with an alternating interference pattern.

FIG. 5 illustrates a PERG projector in which the interferometry optics are based on a Newton's ring interferometer design. A laser projection beam 111 is expanded and collimated as in the embodiment described in Sections 2.1–2.4, and polarized normal to the plane of the FIGURE. The projection beam is reflected from a mirror 112 to a polarizing beam splitter cube 114.

The projection beam is completely reflected by the beam splitter cube through a quarter wave rotating plate 116, toward a Newton's ring interferometer 120 for modulating the beam with a Newton's ring interference pattern. The interferometer is formed by a plano convex lens 122 and an optical flat 124. The plano convex lens has an antireflective (AR) coating on its flat side 122a.

As the projection beam propagates to the left of the beam splitter cube, it is imparted with a circular polarization of one-quarter wave rotation by the quarter wave rotating plate 116. The quarter-rotated projection beam is partially reflected from the plano convex lens 122, and then reflected partially from the optical flat 124. The two reflected beams combine interferometrically to create a PERG interference beam 126 with the Newton's ring interference pattern.

The interference pattern can be alternated (periodically reversing light-dark interference rings) by translating optical flat 124 in a back-and-forth motion along the optical axis. Such translation may be imparted by a conventional electromagnetic mechanism 128 such as a speaker coil diaphragm operating at the desired alternation frequency.

The PERG interference beam, now propagating to the right, is again quarter-rotated by the quarter wave rotating plate 116. The resulting 90° polarization rotation allows the PERG interference beam (i.e., the interference pattern) to pass through the beam splitter cube 114.

The PERG interference beam is directed to segmentation optics formed by a ring aperture 132 and a sectoring aperture 134. The ring aperture allows the ERG pattern to be segmented into, for example, posterior, medial and anterior regions (41, 43 and 42 in FIG. 3). The sectoring aperture allows the interference pattern to be further sectored, for example, along radial lines (45 in FIG. 3).

The selectively segmented PERG interference beam is directed to wide angle imaging optics 140, which include a zoom lens 142 and focusing lenses 144 and 146. The zoom lens adjusts (variably) beam diameter. The pair of focusing lenses (which do not necessarily contact the cornea) have aspheric surfaces which produce extremely short focusing of the beam to a point within eye 150 near the surface of the eye lens 151. After transmitting through the pupil, the light pattern rapidly diverges and is projected onto the retina.

The diameter of the PERG interference beam, and hence the area of the retina onto which the beam is projected, is controlled by the zoom lens 142. Alternatively, the beam can be projected onto the entire retina (including the far periphery), and the ring aperture used to control the region of the retina (posterior, medial and/or anterior) receiving the ERG pattern.

As with the embodiment described in Sections 2.1–2.4, various components of the PERG projector can be controlled by a PERG processor (not shown) executing a PERG program. For example, the PERG processor can control the rate and amplitude of the translation of the optical flat 124, the setting of the sectoring aperture 134, and the magnification of zoom lens 142.

FIG. 6 illustrates an embodiment of the interferometry optics (34 in FIG. 2) based on a Michaelson interferometer design. Interferometry optics 160 includes two mirrors 161, 162 and a beam splitter 163 arranged in a Michaelson interferometer configuration.

The optical path for the mirror 161 includes a Kerr cell 164 to which are attached electric field plates 165. The electric field plates are coupled to a high voltage amplifier 166 controlled by the PERG processor in a manner analogous to the HVA 74 in FIG. 2 (see Section 2.2).

Mirror 161 is stationary while mirror 162 is spring-loaded and pivotally mounted at pivot point 168. Mirror 162 can be selectively pivoted by a motor driven micrometer (MDM) 168. MDM 168 is controlled by the PERG processor in a manner analogous to the MDM 64 in FIG. 2 (see Section 2.2), providing precision angle tuning of the spatial frequency (fringe line spacing) for the interference pattern.

In operation, a collimated projection beam 170 (33 in FIG. 2) is split by splitter 163 into separate beams 171 and 172. Beam 171 passes through the Kerr cell and reflects from mirror 161 passing back through the Kerr cell. Beam 172 reflects from tuning mirror 173 with a slight angular displacement Theta.

The two beams combine at beam splitter 163 to form a projection beam 175 modulated with an interference pattern having a selected spatial frequency determined by the tuning angle Theta. The electric field across the Kerr cell 164 is controlled to modulate the phase of the beam 161 such that the fringes can be made to alternate at a selected frequency, creating the pattern shift that produces a PERG response.

FIG. 7 illustrates an embodiment of the interferometry optics (34 in FIG. 2) based on a pressure controlled interferometer design. Interference pattern modulation is accomplished by selectively varying the index of refraction of a gas media by varying its pressure.

A gas cell 180 replaces the Kerr cell 164 in FIG. 6. The gas cell contains a suitable gas media (such as a fluorocarbon). The pressure of the gas in the cell is controlled by a flexible diaphragm 181 and is modulated by a ferromagnetic plunger 182 moved by an electromagnetic coil 183. Pattern phase modulation is accomplished by controlling the coil current such as with a driver amplifier 185 that responds to control signals from the PERG processor.

3. Alternate Applications

The retinal projection technique of the invention can be used in any application in which images (modulated light) need to be projected into the eye with a field-of-view that can extend into areas that are anterior to the posterior retina, including the far periphery. For example, the retinal projection technique can be used to project video or printed information directly into the eye. Referring to FIG. 2 for such an application, the interferometry modulation optics could be eliminated and the LCD spatial light modulator 86 could be used to modulate the projection beam with video or printed information. This information could be imaged by the wide angle imaging optics 36 onto the entire field-of-view of the retina.

What is claimed is:

1. A retinal projection system for projecting an image onto a selected area of a retina of an eye, said retinal projection system comprising:

a light source for providing a projection beam of at least partially coherent light;

modulation optics for modulating said projection beam with a desired image to form a modulated projection beam; and wide angle imaging optics for focusing said modulated projection beam, whereby said modulated projection beam passes through the pupil of the eye and diverges to project an image on the retina, said image having a field-of-view that includes an area anterior to the posterior 25° of the visual field of the retina.

2. A retinal projection system in accordance with claim 1, wherein said field-of-view of said image includes an area 25°–40° anterior to the posterior-most point of the retina.

3. A retinal projection system in accordance with claim 1, wherein said modulation optics include an aperture for blocking a selected portion of said projection beam, whereby said image is projected onto a selected segment of the retina.

4. A retinal projection system in accordance with claim 1, wherein said modulation optics include an interferometer for modulating said projection beam with an interference pattern to create an ERG pattern, and for selectively alternating said interference pattern to create an ERG pattern shift.

5. An ERG pattern projection (PERG) system for projecting an ERG pattern onto a selected area of a retina of an eye, said PERG system comprising:

a light source for providing a projection beam of at least partially coherent light;

modulation optics for modulating said projection beam to create a desired ERG pattern and for selectively shifting said ERG pattern to create an ERG response from said retina;

imaging optics for focusing said ERG pattern, whereby said ERG pattern passes through the pupil of the eye and diverges to project an ERG pattern image on a selected area of the retina, said ERG pattern image having a field-of-view that includes an area anterior to the posterior 25° of the visual field of the retina.

6. A PERG projection system in accordance with claim 5, wherein said field-of-view of said ERG pattern image includes an area 25°–40° anterior to the posterior-most point of the retina.

7. A PERG projection system in accordance with claim 5, wherein said modulation optics include an interferometer for modulating said projection beam with an interference pattern to form an ERG pattern, and for selectively altering the interference pattern to cause an ERG pattern shift.

8. A PERG projection system in accordance with claim 7, wherein said interferometer modulates said projection beam with a selected spatial frequency to produce a selected fringe line spacing, and with a selected alternation frequency to produce an ERG response from said retina.

9. A PERG projection system in accordance with claim 7, wherein said interferometer is a shearing interferometer comprising:

first and second prisms having a gap therebetween defined by respective first and second opposing, non-parallel prism surfaces formed on said first and second prisms, said first and second opposing, non-parallel prism surfaces defining a shearing angle, said second prism being pivotally mounted relative to said first prism for selectively changing said shearing angle, whereby said projection beam is partially reflected from said first opposing prism surface to form a first reflection beam, and whereby said projection beam, after transiting said gap defined by said first and second opposing, non-parallel prism surfaces, is partially reflected from said second opposing prism surface to form a second reflection beam, such that said first and second reflection beams interferometrically combine to form an interference pattern, and such that said interference pattern is precision angle tuned by selectively changing said shearing angle.

10. The PERG projection system of claim 9, wherein said gap defined by said first and second opposing, non-parallel prism surfaces is filled with a Kerr fluid having a refractive index, and wherein said first and second opposing, non-parallel prism surfaces are coated with transparent conductive electrode layers coupled to a controlled voltage source, such that an adjustable time varying electric field is produced in said gap defined by said first and second opposing, non-parallel prism surfaces for controlling the refractive index of said Kerr fluid so as selectively to shift said interference pattern.

11. A PERG projection system in accordance with claim 7, wherein said interferometer is a Newton's ring interferometer comprising:

a plano convex lens having an antireflective coating on one side thereof and a reflective optical flat, whereby a first portion of said projection beam is reflected by said plano convex lens to form a first reflection beam, and whereby a second portion of said projection beam is reflected by said optical flat to form a second reflection beam, such that the first and second reflection beams interferometrically combine to form an interference pattern.

12. A PERG projection system in accordance with claim 11, said system further comprising a translation means for selectively translating the optical flat to shift the interference pattern.

13. A PERG projection system in accordance with claim 5, further comprising segmentation optics for selectively segmenting said ERG pattern image.

14. A PERG projection system in accordance with claim 13, wherein said segmentation optics comprise:

a ring aperture for segmenting said projection beam into posterior, medial, and anterior regions; and a sectoring aperture for segmenting at least the medial and anterior regions into angular sectors.

15. A PERG projection system in accordance with claim 5, wherein said imaging optics include aspheric surfaces to provide a short focal length.

16. A PERG projection system in accordance with claim 15, wherein the imaging optics include zoom optics for selectively adjusting a diameter of said projection beam.

17. A retinal projection method for selectively projecting an image onto a selected area of a retina, comprising the steps:

generating a projection beam of at least partially coherent light;

modulating said projection beam with a desired image to form a modulated projection beam; and focusing said modulated projection beam, such that said modulated projection beam passes through the pupil of the eye and diverges to project an image on the retina, said image having a field-of-view that includes an area anterior to the posterior 25° of the visual field of said retina.

18. A retinal projection method in accordance with claim 17, wherein said field-of-view of said image includes an area 25°–40° anterior to the poster-most point of the retina.

19. A retinal projection method in accordance with claim 17, said method further comprising the step of blocking a selected portion of said projection beam, such that said image is projected onto a selected segment of the retina.

20. An ERG pattern projection (PERG) method for projecting an ERG pattern onto a selected area of the retina, comprising the steps:
    generating a projection beam of at least partially coherent light;
    modulating said projection beam to create a desired ERG pattern,
    focusing said ERG pattern, such that said ERG pattern passes through the pupil of the eye and diverges to project an ERG pattern image on the retina, said ERG pattern image having a field-of-view that includes an area anterior to the posterior 25° of the visual field of the retina; and
    selectively shifting a phase of said ERG pattern to create an ERG response from said retina.

21. A PERG projection method in accordance with claim 20, wherein said field-of-view of said ERG pattern image includes an area 25°–40° anterior to the posterior-most point of the retina.

22. A PERG projection method in accordance with claim 20, wherein the step of modulating the projection beam comprises the step of modulating said projection beam with an interference pattern to form said ERG pattern.

23. A PERG projection method in accordance with claim 22, wherein said projection beam is modulated with a selected spatial frequency to produce a selected fringe line spacing, and wherein said projection beam is modulated with a selected alternation frequency to produce an ERG response from said retina.

24. A PERG projection method in accordance with claim 20, wherein the step of modulating said projection beam is accomplished by an interferometer.

25. A PERG projection method in accordance with claim 20, further comprising the step of selectively segmenting said ERG pattern.

26. A PERG projection method in accordance with claim 20, further comprising the step of selectively adjusting a diameter of said projection beam.

* * * * *